US012655422B2

(12) United States Patent
Rettig et al.

(10) Patent No.: US 12,655,422 B2
(45) Date of Patent: Jun. 16, 2026

(54) METHODS AND COMPOSITIONS FOR INHIBITION OF CRISPR RE-CLEAVAGE EVENTS

(71) Applicant: Integrated DNA Technologies, Inc., Coralville, IA (US)

(72) Inventors: Garrett R. Rettig, Coralville, IA (US); Nathan Delvaux, Iowa City, IA (US); Ashley M. Jacobi, North Liberty, IA (US); Mollie S Schubert, Cedar Rapids, IA (US); Nathanial Roberts, Iowa City, IA (US); Mark A Behlke, Coralville, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 853 days.

(21) Appl. No.: 17/405,296

(22) Filed: Aug. 18, 2021

(65) Prior Publication Data

US 2022/0056437 A1 Feb. 24, 2022

Related U.S. Application Data

(60) Provisional application No. 63/067,797, filed on Aug. 19, 2020.

(51) Int. Cl.
| | |
|---|---|
| *C12N 15/11* | (2006.01) |
| *C12N 9/22* | (2006.01) |
| *C12N 15/90* | (2006.01) |

(52) U.S. Cl.
CPC ............... *C12N 15/11* (2013.01); *C12N 9/22* (2013.01); *C12N 15/907* (2013.01); *C12N 2310/20* (2017.05); *C12N 2310/315* (2013.01); *C12N 2310/321* (2013.01); *C12N 2310/322* (2013.01); *C12N 2310/3231* (2013.01)

(58) Field of Classification Search
None
See application file for complete search history.

(56) References Cited

U.S. PATENT DOCUMENTS

| | | | | |
|---|---|---|---|---|
| 2019/0300872 A1* | 10/2019 | Woolf | .................... | C12N 15/09 |
| 2019/0345479 A1* | 11/2019 | Mello | ...................... | C12N 9/22 |
| 2020/0040362 A1* | 2/2020 | Carlo | .................... | C12N 15/111 |
| 2021/0079387 A1* | 3/2021 | Skarnes | ............... | C12N 15/907 |
| 2021/0123035 A1* | 4/2021 | Woodley | .............. | C12N 15/113 |

OTHER PUBLICATIONS

Skarnes et al (Methods, 2019, 164-165; p. 18-28).*
Papaioannou et al (Expert Opinion on Biological Therapy, 2012, 12:329-342).*
International Search Report and Written Opinion for International Application No. PCT/US2021/046465 dated Jan. 19, 2022.
Jacobi, A.M., et al. Simplified CRISPR tools for efficient genome editing and streamlined protocols for their delivery into mammalian cells and mouse zygotes. Methods. May 15, 2017:121-122.
Rose, J.C., et al. Suppression of unwanted CRISPR-Cas9 editing by co-administration of catalytically inactivation truncated guide RNAs. Nature Communications. 11:2697 (2020).

* cited by examiner

*Primary Examiner* — Laura B Goddard
(74) *Attorney, Agent, or Firm* — Potomac Law Group, PLLC; Reza Mollaaghababa; Joseph F. Murphy

(57) ABSTRACT

The disclosure relates to methods and compositions that serve to reduce the potential for targeted nuclease activity for example, but not limited to, CRISPR enzymes such as Cas9 and/or Cas12a. The disclosure also relates to methods and compositions be used as an HDR substrate to prevent Cas9 re-cleavage, and as a result increase the frequency of perfect HDR.

13 Claims, 6 Drawing Sheets

Specification includes a Sequence Listing.

FIG. 3
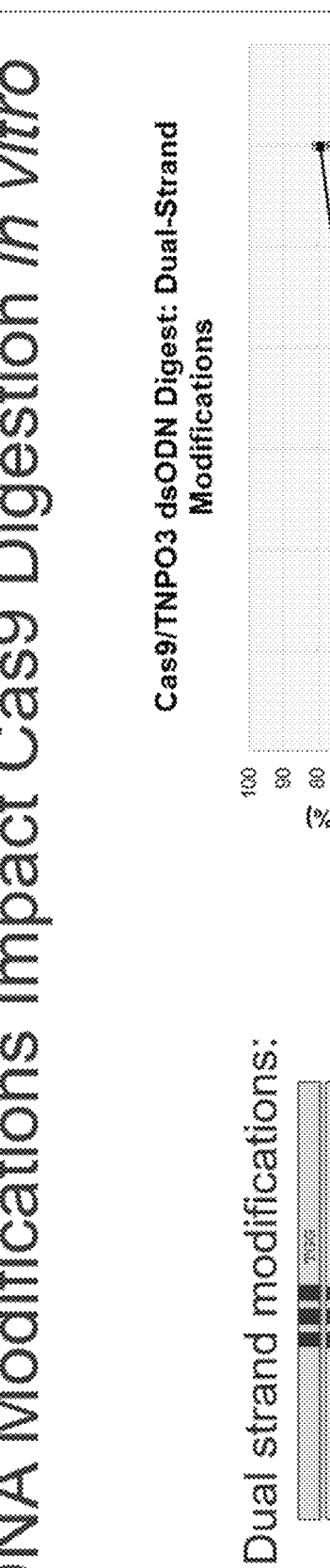
DNA Modifications Impact Cas9 Digestion *in vitro*
- Dual strand modifications:
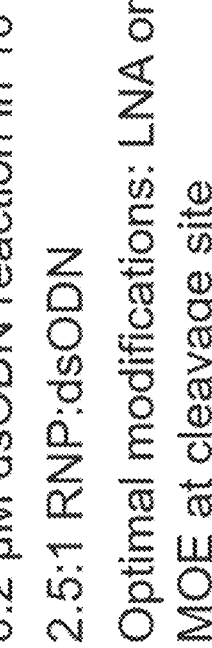
- 0.2 µM dsODN reaction in 10 µL
- 2.5:1 RNP:dsODN
- Optimal modifications: LNA or MOE at cleavage site
Cas9/TNPO3 dsODN Digest: Dual-Strand Modifications
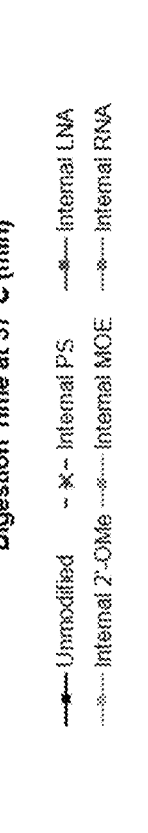
Percent Digested (%)
Digestion Time at 37°C (min)
Unmodified    Internal PS    Internal LNA
Internal 2'-OMe    Internal MOE    Internal RNA

FIG. 5

Cas9 Digestion *in vitro*: Variable Mod. Number and Location

- TS Single-strand modifications:

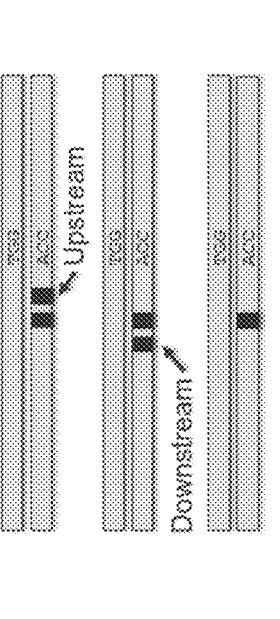

- Included combined MOEPS modification with PS at cut site

- Optimal modifications: 2 MOE or 1 MOEPS either upstream/downstream

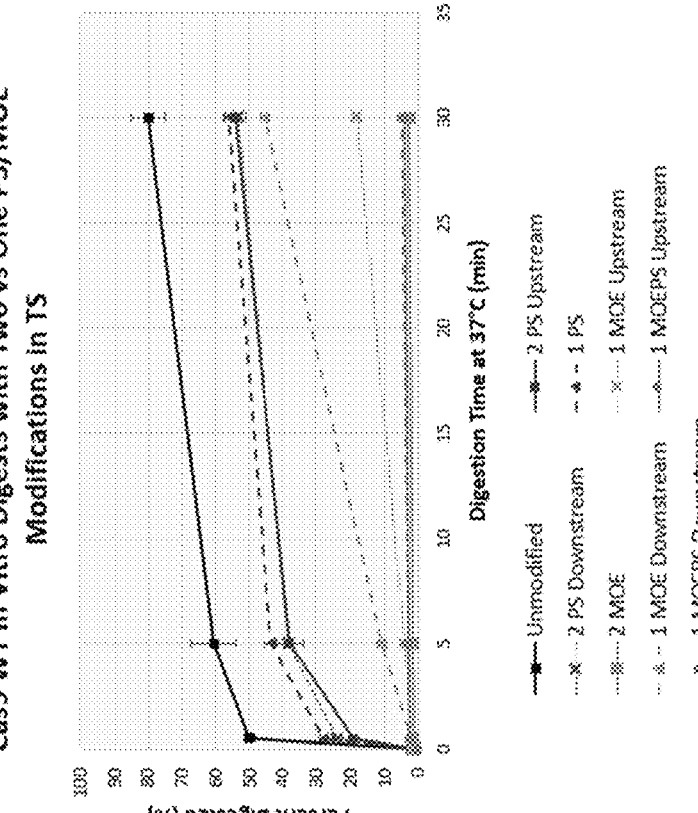

Cas9 WT In Vitro Digests with Two vs One PS/MOE Modifications in TS

Percent Digested (%)

Digestion Time at 37°C (min)

— Unmodified
✕ 2 PS Downstream
···· 2 MOE
▲ 1 MOE Downstream
✱ 1 MOEPS Downstream
— 2 PS Upstream
▲ 1 PS
✕ 1 MOE Upstream
▲ 1 MOEPS Upstream FIG. 6
Cas9 Digestion *in vitro*: Variable Mod. Number and Location
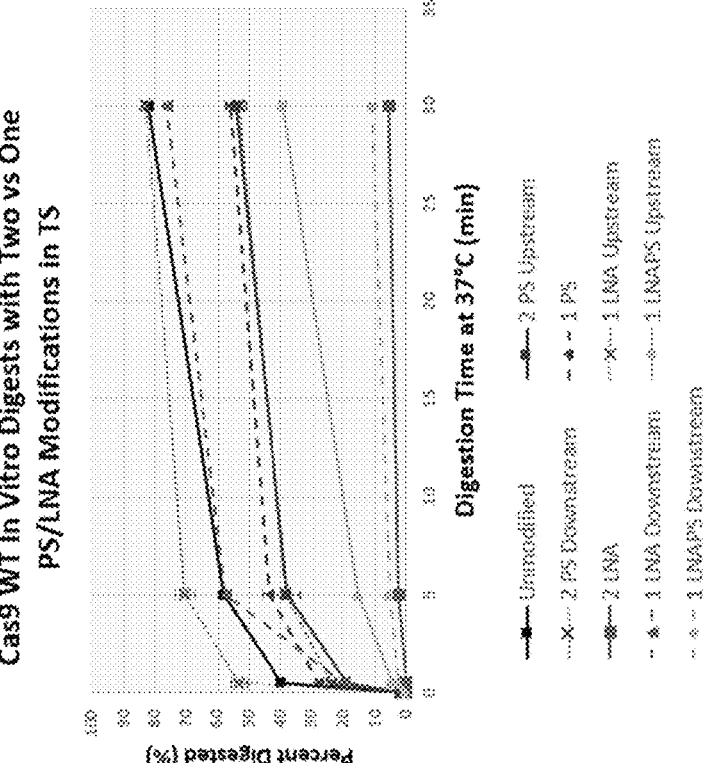
- TS Single-strand modifications:
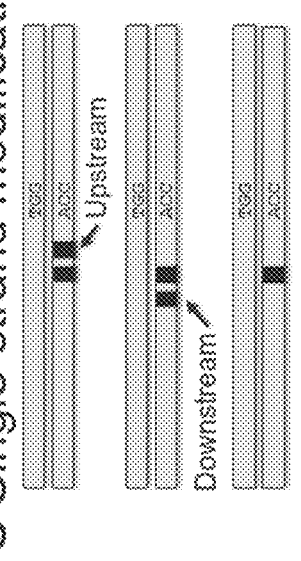
- Included combined LNAPS modification with PS at cut site
- Optimal modification: 1 LNAPS Downstream

SEQUENCE LISTING

```
<160> NUMBER OF SEQ ID NOS: 7

<210> SEQ ID NO 1
<211> LENGTH: 132
<212> TYPE: DNA
<213> ORGANISM: Artificial Sequence
<220> FEATURE:
<223> OTHER INFORMATION: Primer

<400> SEQUENCE: 1
cctgaatacg acctaatagc tgtttccgag ggggcaactt ccacggagag ccttctgccc        60
tggtaacggc caaagaggag gagatggcgc cagtcaggga gcggccgtgg cccagacagt       120
gaggaagcgc ga                                                           132

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
ccacggagag ccttctgccc tgg                                                23

<210> SEQ ID NO 3
```

-continued

```
<211> LENGTH: 23
<212> TYPE: DNA
<213> ORGANISM: Artificial Sequence
<220> FEATURE:
<223> OTHER INFORMATION: Primer

<400> SEQUENCE: 3
ccacggagag ccttctgccc tgg                                        23

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ccacggagag cctgccctgg                                            20

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ccacggagag ccttctgccc tgg                                        23

<210> SEQ ID NO 6
<211> LENGTH: 23
<212> TYPE: RNA
<213> ORGANISM: Artificial Sequence
<220> FEATURE:
<223> OTHER INFORMATION: Primer

<400> SEQUENCE: 6
ccacggagag ccuucugccc ugg                                        23

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ccacggagag ccttctgccc                                            20
```

METHODS AND COMPOSITIONS FOR INHIBITION OF CRISPR RE-CLEAVAGE EVENTS

CROSS REFERENCE TO RELATED APPLICATIONS

This application claims priority to U.S. Provisional Patent Application No. 63/067,797 filed Aug. 19, 2020, the contents of which are incorporated by reference herein in its entirety.

FIELD OF THE DISCLOSURE

The disclosure relates to methods and compositions that serve to reduce the potential for targeted nuclease activity for example, but not limited to, CRISPR enzymes such as Cas9 and/or Cas12a. The disclosure also relates to methods and compositions for use as an HDR substrate to prevent Cas9 re-cleavage, and as a result increase the frequency of perfect HDR.

BACKGROUND

Specific, desired repair outcomes can be made in genomic DNA when targeted nuclease-mediated cleavage events, for example Cas9 or Cas12a, are co-delivered intracellularly with a homology-directed repair (HDR) substrate. The HDR substrate may be a single-stranded, synthetic DNA oligonucleotide typically containing 40-bp homology arms (HAs); however, they could also include ssDNA templates with shorter homology arms, enzymatically-generated ssDNA templates with larger insertions (>1 kb) and larger HAs (>500 bp), viral-derived ssDNA substrates, or dsDNA repair templates that are enzymatically-generated with similarly large insertions and HAs.

A common short-coming in achieving specific repair outcomes via HDR is the Cas9 re-cleavage (or re-cutting) event to give imperfect HDR rather than perfect HDR. This is particularly common when the editing event does change any of the 23-bp comprising the PAM/protospacer sequence or when the edit is small enough so as to not significantly disrupt the ribonucleoprotein (RNP) complex from mediating a double-stranded break (DSB) in the HDR product. Without being bound to any specific theory it is hypothesized that the partial HDR event occurs as follows: 1) the RNP complex mediates a DSB, 2) the DSB is repaired via HDR in the presence of a donor template, 3) still present in the cell, the RNP complex is able to bind and cleave (re-cleave or re-cut) at the uninterrupted PAM/protospacer to generate another DSB, and 4) this additional DSB is repaired via NHEJ often resulting in a small INDEL at the Cas9 cleavage site in addition to the already-present HDR event.

Other strategies involved in reducing re-cleavage events revolved around the incorporation of "silent" mutations in the PAM/protospacer sequence. These silent mutations incorporate single nucleotide variations or SNPs within the PAM/protospacer sequence of the HDR donor template. However, there are potential detriments to using the silent mutation strategy. For example, when the edit along with silent mutations are incorporated into the coding region of a gene, so-called silent mutations may have unpredictable and unintended consequences on mRNA splicing. In addition, in non-coding regions, it is difficult to predict if a mutation will truly be silent, as the expanded functions of non-coding, 'junk DNA' are continuing to be understood. Additional strategies incorporate cold shock procedures or the use of small molecule HDR enhancers to boost HDR frequency, but again these methods do not reduce the re-cleavage events.

Another strategy related to scarless HDR, or perfect HDR, that reduces re-cleavage events rely on the introduction of shorter gRNAs that would bind, but never cleave the perfect HDR event (truncated guide RNAs that direct Cas9 binding but no clevage). Though this could be an effective strategy, this advancement by Rose, et al. published in *Nature Communications* would seem to apply only to the scenario where the HDR mutation is within ~16-bp of the PAM sequence and would thus allow for Cas9 targeting/blocking of re-cleavage with the truncated gRNA+protein complex.

What is needed are methods and compositions that directly reduce the frequency of re-cleavage. Further, the ability to incorporate ssDNA donors into the genome to inhibit Cas9 re-cleavage events and facilitate perfect DNA replication during cell division is needed.

SUMMARY

The disclosure relates to methods and compositions that serve to reduce the potential for targeted nuclease activity for example, but not limited to, CRISPR enzymes such as Cas9 and/or Cas12a. The disclosure also relates to methods and compositions to be used as an HDR substrate to prevent Cas9 re-cleavage, and as a result increase the frequency of perfect HDR.

In one aspect the disclosure provides single-stranded DNA oligonucleotides used as homology-directed repair donor templates that contain internally modified nucleotides or internally-modified phosphodiester linkages that serve to reduce the potential for targeted nuclease activity (Cas9, Cas12a, etc) by positioning the chemical modifications adjacent to the canonical nuclease cleavage site In another aspect the disclosure provides for the use of internal chemical modifications to single-stranded DNA substrates for HDR to inhibit endonuclease activity, but the modifications are not necessarily limited to CRISPR-mediated, HDR events. These can be more broadly viewed as DNA substrates that inhibit nuclease activity.

In another aspect These oligonucleotides could be used as HDR donor templates (for Cas9, Cas12a or other Cas proteins) that makes the specific, desired edit in genomic DNA, yet also preserves the WT sequence at the cut site. This is particularly necessary when the desired edit is either outside of the protospacer sequence or if the edit is not significant enough to disrupt the nuclease activity by lowering the activation energy of substrate cleavage via introduction of mismatches.

In another aspect these oligonucleotides containing internal modifications could be used in HDR ad-mixing experiment of two (or more) ssDNA HDR donors to preserve WT (wild-type) alleles using WT-internally-modified oligos that are resistant to cleavage yielding DSBs and subsequent repair via NHEJ. The co-delivery and dual repair outcomes preserves WT to a greater degree than a single ssDNA approach, but also is expected to show bi-allelic editing outcomes.

In another aspect in vitro approaches suggest that the internally modified oligonucleotides can serve to inhibit, in a competitive fashion, any sequence-specific nuclease activity (via a guided nuclease such as Cas9, Cas12a, etc or a sequence-specific restriction endonuclease). Similarly, the use of a modified substrate that is recognized by a Cas protein, but not cleaved, could be used to selectively inhibit undesired effects—like off-target editing events or Cas9 re-cleavage—that might be mediated by a Cas protein intracellularly.

Specific embodiments of the disclosure will become evident from the following more detailed description and the claims.

BRIEF DESCRIPTION OF THE DRAWINGS

FIG. 3 shows internal modification on both strands of the duplexed DNA oligonucleotides results in varying degrees of inhibition of Cas9 cleavage. Compared to unmodified oligonucleotides, the following relationship shows the performance of internal modifications in Cas9 inhibition after 30 minutes: Unmodified=RNA<PS<2'-OMe<LNA=MOE.

FIG. 5 shows Cas9 digestion of double-stranded DNA with variable number of MOE and MOE-PS modifications and change in positions on the targeting strand.

FIG. 6 shows Cas9 digestion of double-stranded DNA with variable number of LNA and LNA-PS modifications and change in positions on the targeting strand

DETAILED DESCRIPTION

Figure 1:
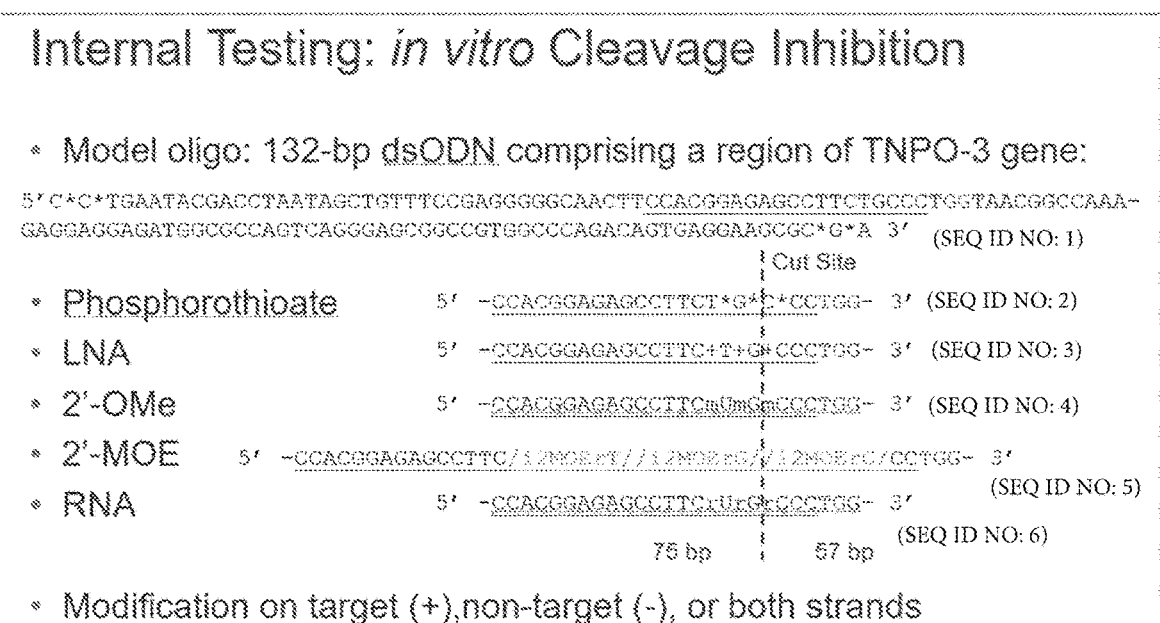
FIG. 1 provides a description of oligonucleotides used in the in vitro assay and placement of modified nucleotides (at positions 3, 4 and 5 upstream from the PAM sequence, which is situated 3' of the protospacer as shown in FIG. 1) and modified linkages (linking positions 2-3, 3-4, 4-5 with respect to the PAM). In this assay, Cas9 targets the dsDNA duplex of 132-bp and the cleavage products are resolved as 75-bp and 57-bp dsDNA species in order to determine the %-cleavage at time points from 0-30 minutes

The disclosure relates to methods and compositions which reduce the potential for targeted nuclease activity for example, but not limited to, CRISPR enzymes such as Cas9 and/or Cas12a. The disclosure also relates to methods and compositions be used as an HDR substrate to prevent Cas9 re-cleavage, and as a result increase the frequency of perfect HDR.

Reference will now be made in detail to exemplary embodiments of the claimed invention. While the claimed invention will be described in conjunction with the exemplary embodiments, it will be understood that it is not intended to limit the claimed invention to those embodiments. To the contrary, it is intended to cover alternatives, modifications, and equivalents, as may be included within the spirit and scope of the claimed invention, as defined by the appended claims.

Those of ordinary skill in the art may make modifications and variations to the embodiments described herein without departing from the spirit or scope of the claimed invention. In addition, although certain methods and materials are described herein, other methods and materials that are similar or equivalent to those described herein can also be used to practice the claimed invention.

In addition, any of the compositions or methods provided, disclosed, or described herein can be combined with one or more of any of the other compositions and methods provided, disclosed, or described herein.

Definitions

Unless defined otherwise, all technical and scientific terms used herein have the meaning commonly understood by a person skilled in the art to which the claimed invention belongs. The terminology used herein is for describing particular embodiments only and is not intended to be limiting of the claimed invention. All technical and scientific terms used herein have the same meaning.

The following terms may have meanings ascribed to them below, unless specified otherwise. However, it should be understood that other meanings known or understood by those having ordinary skill in the art are also possible, and within the scope of the claimed invention. All publications, patent applications, patents, and other references mentioned or discussed herein are expressly incorporated by reference in their entireties. In the case of conflict, the present specification, including definitions, will control. In addition, the materials, methods, and examples are illustrative only and not intended to be limiting.

As used herein, the singular forms "a," "and," and "the" include plural references, unless the context clearly dictates otherwise.

As used herein, the term "or" means, and is used interchangeably with, the term "and/or," unless context clearly indicates otherwise.

As used herein, the term "including" means, and is used interchangeably with, the phrase "including but not limited to."

As used herein, the term "such as" means, and is used interchangeably with, the phrase "such as, for example" or "such as but not limited."

Unless specifically stated or obvious from context, as used herein, the term "about" is understood as within a range of normal tolerance in the art, for example, within two standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The term "decreased," as used herein with regard to the re-cleavage of target genomic regions, refers to the level of cutting by guided endonuclease systems, such as CRISPR system after incorporation of the modified HDR donor. A guided endonuclease system has "decreased" re-cleavage activity if the level of its cleavage activity, as measured by the cleavage assay or as measured by other methods known in the art is less than the base cleavage activity before introduction of the modified HDR donor. For example, the re-cleavage activity of the guided endonuclease system is decreased if the re-cleavage activity is at least 95%, 90%, 85%, 80%, 75%, 70%, 65%, 60%, 55%, 50%, 45%, 40%, 35%, 30%, 25%, 20%, 15%, 10%, or 5% less than, or at least 2-fold, 3-fold, 4-fold, 5-fold, 10-fold, or more than 10-fold less than the base cleavage activity before introduction of the modified HDR donor.

As used herein the term "imperfect HDR" are those HDR events which occur when the DSB is repaired, as intended, by adding the desired change in the single stranded donor oligo. However, the intended sequence is subsequently re-cut (re-cleaved) by the CRISPR system and then repaired by a NHEJ mechanism at the cut site. In the context of double-stranded HDR donors imperfect HDR refers to the blunt integration, reverse integration, or concatameric liga-tion events.

As used herein the term "perfect HDR" can be described as a repair outcome that reflects only the intended change to the target genomic sequence.

EXAMPLES

The claimed invention is further illustrated by the follow-ing Examples, which should not be construed as limiting. Those of skill in the art will recognize that the claimed invention may be practiced with variations of the disclosed structures, materials, compositions, and methods, and such variations are regarded as within the scope of the claimed invention.

Example 1. Methods to Digest and Resolve the CRISPR Products on a Fragment Analyzer (Agilent Technologies)

Figure 2:
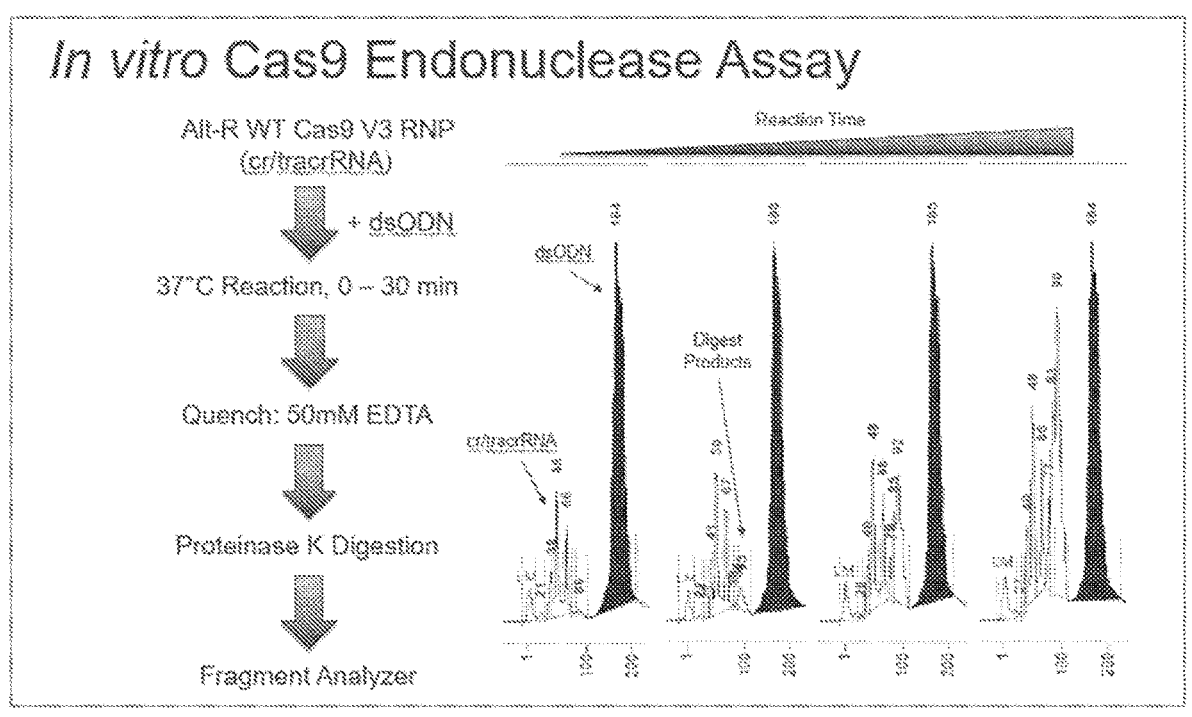
FIG. 2 shows workflow for digestion through analysis of cleavage products to determine the percent of the dsDNA substrate that is digested and, by extension, the degree to which the internal modifications are inhibiting digestion via S.p. Cas9.

FIG. 2 shows a typical workflow for visualizing CRIPSR editing experiments. The typical workflow is as follows:
1. DNA substrate duplexes from 132-nt oligos were combined in equal-mole amounts in IDT duplex buffer, heated to 95 C and cooled to room temperature at 10 uM final concentration.
2. The Cas9 digest reactions were carried out in BioRad 96-well, full-skirted plates at 37 C. Components in the 10 ul reaction include 1× Cas9 reaction buffer (from 5× stock), 2 pmol of dsDNA substrate, and 5 pmol RNP complex (1:1 mol ratio of v3 Cas9:gRNA formed as discussed previously in Jacobi, et al).
3. Reactions were quenched at 0, 0.5, 5 and 30 minutes with 2 ul of 300 mM EDTA (50 mM final concentra-tion). Cas9 was digested with proteinase K (1 ul of 20 mg/ml solution) for 10 minutes at 56 C. Samples were further diluted with 60.85 ul of nuclease-free water and vortexed.
4. Reaction products were resolved via capillary electro-phoresis on the Fragment Analyzer via CRP-910-33 CRISPR Discovery method, dsDNA 810 gel with 180 s vacuum injection time.
5. Calculations for % cleavage from band intensities were calculated as follows: 100×((Digested product 1+Di-gested product 2)/(Digested product 1+Digested prod-uct+Full length product)).

Example 2. Dual Strand Internal Modifications and the Effect on the Reduction of CRISPR Re-Cleavage Events In initial experiments, both of the duplexed oligonucle-otides, comprising the targeting and non-targeting strands, contained the modified nucleic acids at the locations indi-cated in FIG. 1. Unmodified oligonucleotides as well as the RNA (ribonucleic acid)-modified oligonucleotides showed very similar cleavage kinetics and gave >70% digestion after 30 minutes under the previously discussed reaction condi-tions. The dsDNA substrates containing the phosorothioate (PS) modified linkages reduced cleavage activity by about 50%. The internal 2'-OMe (2'-O-methyl-RNA) modifica-tions reduced the cleavage activity to 14.5%. Both the LNA (locked nucleic acid)-modified oligonucleotides and the MOE (2'-O-methoxyethly RNA)-modified oligonucleotides gave <2% digestion (FIG. 3).

Figure 4:
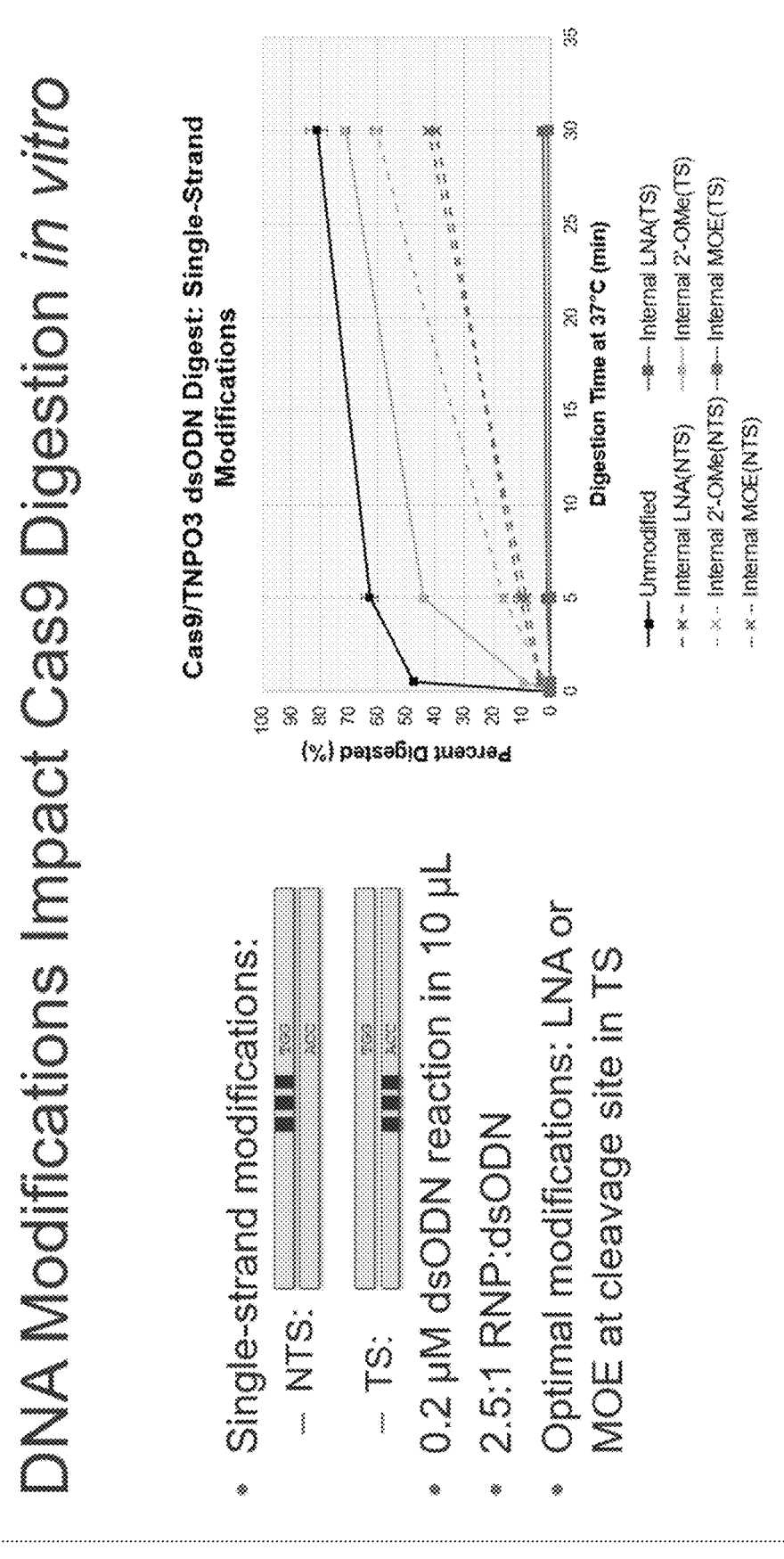
FIG. 4 demonstrates Cas9 digestion of double-stranded DNA with single-strand modifications showing that the MOE modification and the LNA modification provide the greatest inhibition of Cas9 re-cleavage when the modifications are positioned on the targeting strand and paired with an unmodified non-targeting strand.

Example 3. Single Strand Internal Modifications and the Effect on the Reduction of CRISPR Re-Cleavage Events After examining the inhibitory activity of the dual-strand modifications the impact of duplexed DNA comprised of one modified and one unmodified strand on Cas9 cleavage inhibition was assessed. In this example, the modifications with dual-strand inhibition, 2'-OMe, LNA and 2'-MOE, were again compared to an unmodified dsDNA substrate; how-ever, the modifications were placed on either the targeting strand or the non-targeting strand of the gRNA in order to understand the impact of the single-stranded modifications on in vitro cleavage. In FIG. 4, the MOE and the LNA modifications placed on the targeting strand confer almost 100% resistance to cleavage with WT Cas9; whereas, the same modifications on the non-targeting strand (cleaved by the RuvC nuclease domain) only give about 50% inhibition compared to the percent digestion observed for the unmodi-fied duplex. Although the inhibitory effect from the 2'-OMe modifications is reduced, it is notable that the modified nucleotides on the non-targeting strand lead to a reduction in Cas9 digestion which is greater than the reduction in diges-tion mediated by the targeting strand, giving 60% digestion and 71% digestion, respectively.

Example 4. Single Strand and Single Internal Modifications and the Effect on the Reduction of CRISPR Re-Cleavage Events As shown in Example 3 the MOE and LNA modifications on the targeting strand provided an almost 100% inhibition of Cas9 cleavage out to 30 minutes (FIG. 4). In Example 4 modified oligonucleotides with a varied number of internal modifications were designed. Example 4 further demon-strates the minimal requirement for modifications that inhibit Cas9 cleavage. In both cases of a single MOE modification along with a single phosphorothioate modifi-cation (where "MOEPS upstream" has a PS-linkage between nucleotide positions 3 and 4 from the PAM sequence and a MOE modification at nucleotide position 3 and "MOEPS downstream" has a PS linkage at the same location but a MOE modification of the nucleotiede at position 4), it is apparent that a single nucleotide modification at a nucleotide adjacent to the cut-site paired with a PS-linkage at the canonical Cas9 cleavage site represent the minimally suffi-cient modifications to fully inhibit Cas9 cleavage in vitro. (FIG. 5).

Interestingly, the single LNAPS (LNA modification with a single PS) modification (FIG. 6) demonstrates some inhi-bition of Cas9 cleavage in either the upstream or down-stream position. However, the "2-LNA" substrate, with positions 3 and 4 modified by LNAs, is the modification that gives the greatest inhibition in this experiment.

Example 5. Testing of Modified ssDNA HDR in Cells

Finally, the modified ssDNA HDR donor templates were tested in cells. In this example, each donor template represented the WT sequence. In this example, if the donor template is incorporated, this should represent the most likely scenario for re-cleavage to occur following repair, that is, one in which the repaired product remains a perfect match for the co-delivered RNP complex. The cell culture and nucleofection methods follow.

The cell culture and nucleofection methods employed here are as follows. HEK293 cells were transfected with 2 μM S.p Cas9 v3 RNP targeting TNPO3 (guide RNA sequence: 5'-CCACGGAGAGCCTTCTGCCC-3') (SEQ ID NO: 7) along with 2 μM IDT Alt-R Electroporation Enhancer, and varying dose of ssDNA HDR donor templates (0.1, 0.5, 1.0, 2.0, 3.2 μM). Ribonucleoprotein complexes (RNP) and single-stranded oligodeoxynucleotide (ssODN) or modified ssDNA HDR donor templates were delivered to HEK293 cells using the Amaxa Nucleofector System by Lonza. Cells were counted and pelleted using centrifugation. The pelleted cells were washed with 10 mL 1× phosphate-buffered saline (PBS). The cells were pelleted again and resuspended in Nucleofection Solution. Alt-R CRISPR-Cas9 crRNA/tracrRNA targeting the TNPO3 site was assembled as an RNP complex as described in Jacobi, et al. For each electroporation, 5 μL of RNP complex was added to 20 μL of cells in Nucleofection Solution (3-5E5 cells/nucleofection). A single-stranded Ultramer DNA oligo consisting 40-nucleotide (nt) arms of homology flanking the genomic DNA cut site were designed to retain the WT genomic DNA sequence. Donor DNA and IDT Alt-R Cas9 Electroporation Enhancer were added to the reaction to the final concentrations noted above in a final volume of 28 μL PBS. The reaction was mixed by pipetting and 25 μL was transferred to an electroporation cuvette plate. The cells were electroporated according to the manufacturer's protocol for this cell line. After electroporation, the cells were resuspended in 75 μL pre-warmed culture media in the electroporation cuvette. Triplicate aliquots of 25 μL of resuspended cells were further cultured in 175 μL pre-warmed media. The cells were allowed to grow until 100% confluency, 48-72 hours in total, after which genomic DNA was isolated via Quick Extract Buffer (Epicentre). The percent wild-type sequence as well as the percent of NHEJ repair for each treatment was quantified by NGS amplicon sequencing on the Illumina MiSeq platform and data analysis done via IDT's in-house data analysis pipeline (rhAmpSeq, CRISP-Alt-Rations).

Figure 7:
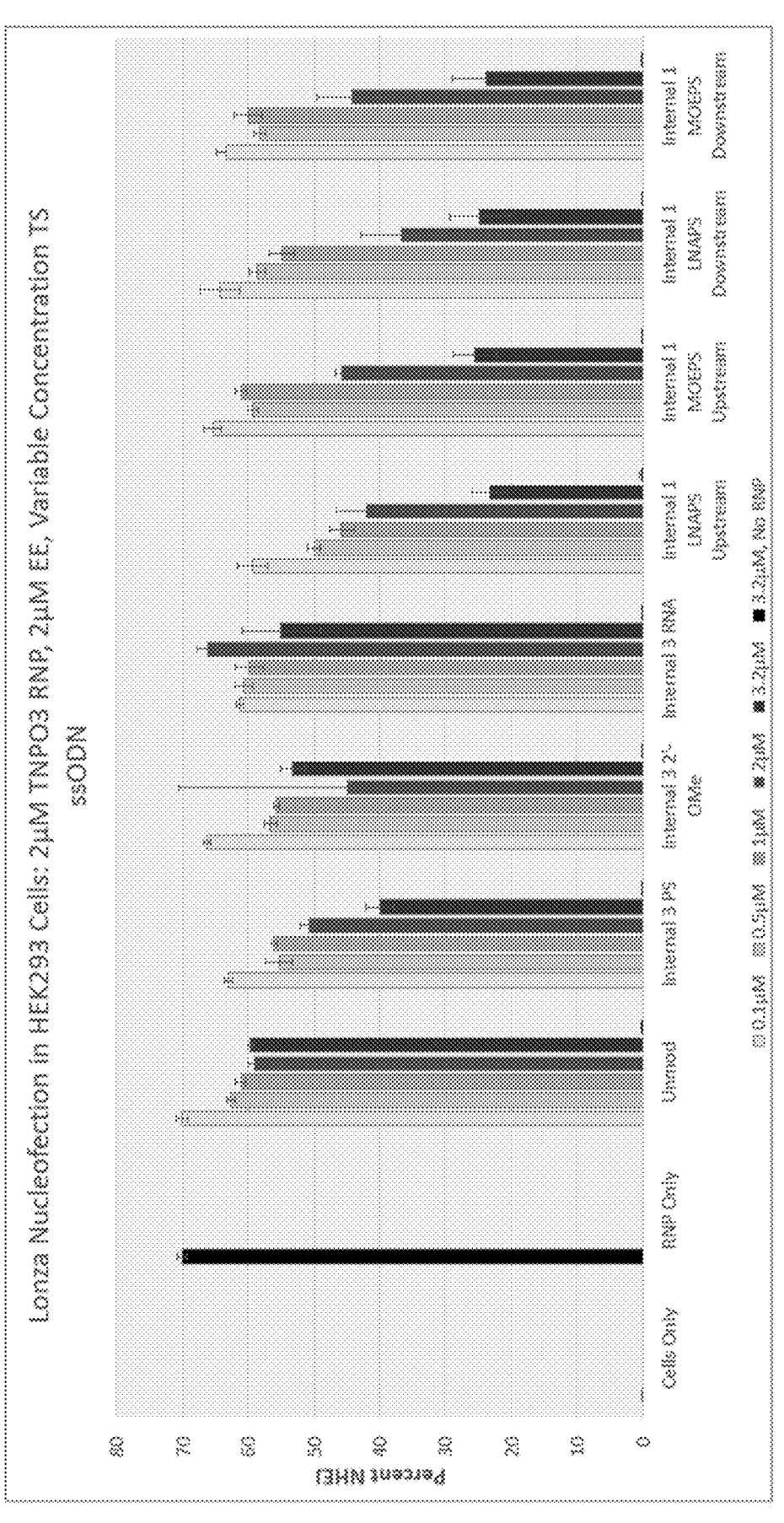
FIG. 7 shows editing in HEK293 cells in which NHEJ is reduced and the native, wild-type sequence is preserved with modified HDR donor templates. Templates contain the native gDNA sequence and reduce NHEJ in a dose-dependent fashion with the presence of modified nucleotides that inhibit Cas9 re-cleavage.

FIG. 7, shows the results graphed with "Percent NHEJ" as the readout on the y-axis. As can be seen, the "RNP-only" condition, which lack a ssDNA donor, as well as the "Unmod" donor condition result in 60-70% NHEJ, and the unmodified DNA donor does not confer much Cas9 cleavage inhibition. In contrast, we observe >50% inhibition of NHEJ in the 3.2 μM ssDNA delivery condition for both MOEPS and LNAPS variables tested. In a dose-response fashion, the results suggest that internally-modified ssDNA HDR donors are incorporated into the genome of HEK293 cells and confer a resistance to S.p. Cas9 re-cleavage

Bibliography

Jacobi, et al. Methods. May 15, 2017:121-122. *Simplified CRISPR tools for efficient genome editing.*

Skarnes, et al. Methods. Jul. 15, 2019: 164-165. *Improving homology-directed repair efficiency in human stem cells.*

Rose, et al. Nature Communications. 11:2697 (2020). *Suppression of unwanted CRISPR-Cas9 editing by co-administration of catalytically inactivation truncated guide RNAs.*

What is claimed is:

1. A modified double stranded DNA homology directed repair (HDR) donor comprising:

a targeting strand comprising one or more internal chemical modifications selected from the group consisting of: Locked Nucleic Acid (LNA), 2'-O-methoxyethyl (2'-MOE), and 2'-O-methyl (2'-OMe), and further wherein the one or more internal chemical modifications are adjacent to the endonuclease cleavage site;

a non-targeting strand, wherein the non-targeting strand lacks the one or more internal chemical modifications comprised by the targeting strand, wherein the one or more internal chemical modifications on the targeting strand reduces a nuclease-mediated re-cleavage and improves HDR efficiency.

2. The modified HDR donor of claim 1, wherein the one or more internal chemical modifications are placed upstream of a CRISPR PAM recognition sequence.

3. The modified HDR donor of claim 2, wherein the one or more internal chemical modifications are placed 2, 3, 4, or 5 bases upstream of the CRISPR PAM recognition sequence.

4. The modified HDR donor of claim 1, wherein the one or more internal chemical modifications comprises 2'MOE.

5. The single stranded HDR donor of claim 1, wherein the one or more internal chemical modifications comprises LNA.

6. The single stranded HDR donor of claim 4, wherein the nuclease-mediated re-cleavage is mediated by Cas9 or Cas12a.

7. The modified HDR donor of claim 1, wherein the modified HDR donor further comprises phosphorothioate internucleotide linkages.

8. A method for reducing targeted nuclease re-cleavage events comprising:

contacting a candidate editing target locus site with an active CRISPR endonuclease system comprising a nuclease, a guide RNA, and the modified HDR donor of claim 1.

9. The method of claim 8, wherein the modified HDR donor comprises one or more internal chemical modifications selected from the group consisting of: LNA and 2'-MOE.

10. The method of claim 9, wherein the one or more internal chemical modifications are placed 2, 3, 4, or 5 bases upstream of the CRISPR PAM recognition sequence.

11. The method of claim 9, wherein the one or more internal chemical modifications comprises 2'MOE.

12. The method of claim 9, wherein the one or more internal chemical modifications comprises LNA.

13. The method of claim 9, wherein the modified HDR donor further comprises phosphorothioate internucleotide linkages.

\* \* \* \* \*